United States Patent
Berlanga Acosta et al.

(10) Patent No.: US 11,564,975 B2
(45) Date of Patent: Jan. 31, 2023

(54) USE OF GHRP-6 AS LATE CARDIOPROTECTIVE AND CARDIAC RESTORATION MEDICAMENT

(71) Applicant: Centro de Ingeniería Genética y Biotecnología, Havana (CU)

(72) Inventors: Jorge Amador Berlanga Acosta, Havana (CU); Gerardo Enrique Guillén Nieto, Havana (CU); Diana Garcia Del Barco Herrera, Havana (CU); Francisco Hernández Bernal, Havana (CU); Sonia Gonzalez Blanco, Havana (CU); Raimundo Ubieta Gómez, Havana (CU)

(73) Assignee: Centro de Ingeniería Genética y Biotecnología, Havana (CU)

( * ) Notice: Subject to any disclaimer, the term of this patent is extended or adjusted under 35 U.S.C. 154(b) by 0 days.

(21) Appl. No.: 17/269,874

(22) PCT Filed: Aug. 19, 2019

(86) PCT No.: PCT/CU2019/050007
§ 371 (c)(1),
(2) Date: Feb. 19, 2021

(87) PCT Pub. No.: WO2020/038499
PCT Pub. Date: Feb. 27, 2020

(65) Prior Publication Data
US 2021/0252109 A1    Aug. 19, 2021

(30) Foreign Application Priority Data
Aug. 21, 2018 (CU) ................... 2018-0093

(51) Int. Cl.
*A61K 38/25* (2006.01)
*A61P 9/10* (2006.01)
*A61K 9/00* (2006.01)

(52) U.S. Cl.
CPC ............ *A61K 38/25* (2013.01); *A61K 9/0019* (2013.01); *A61P 9/10* (2018.01)

(58) Field of Classification Search
None
See application file for complete search history.

(56) References Cited

FOREIGN PATENT DOCUMENTS

WO    2002053167 A2    7/2002

OTHER PUBLICATIONS

Iwase et al. "Growth hormone-releasing peptide can improve left ventricular dysfunction and attenuate dilation in dilated cardiomyopathic hamsters," Cardiovascular Research 61 (2004) 30-38 (Year: 2004).*

Arós, Fernando, et al. "Guías de Práctica Clínica de la Sociedad Española de Cardiología en Pruebas de Esfuerzo," Revista Española de Cardiología, vol. 53.8, pp. 1063-1094 (2000). (Abstract Only, Part1).
Arós, Fernando, et al. "Guías de Práctica Clínica de la Sociedad Española de Cardiología en Pruebas de Esfuerzo," Revista Española de Cardiología, vol. 53.8, pp. 1063-1094 (2000). (Abstract Only, Part2).
"Cardiovascular Diseases (CVDs) Key Facts", World Health Organization, May 17, 2017. http://www.who.int/en/new-room/fact-sheet/detail/cardiovascular-diseases-(cvds).
Antman, E. M., et al. "ACC/AHA Guidelines for the Management of Patients with ST-Elevation Myocardial Infarction—Executive Summary: A Report of the American College of Cardiology/American Heart Association Task Force on Practice Guidelines (Writing Committee to Revise the 1999 Guidelines for the Management of Patients with Acute Myocardial Infarction," Circulation, vol. 110.5 pp. 588-636 (2004). DOI:10.1161/01.CIR.0000134791.68010.FA (Part1).
Antman, E. M., et al. "ACC/AHA Guidelines for the Management of Patients with ST-Elevation Myocardial Infarction—Executive Summary: A Report of the American College of Cardiology/American Heart Association Task Force on Practice Guidelines (Writing Committee to Revise the 1999 Guidelines for the Management of Patients with Acute Myocardial Infarction," Circulation, vol. 110.5 pp. 588-636 (2004). DOI:10.1161/01.CIR.0000134791.68010.FA (Part2).
Antman, E. M., et al. "ACC/AHA Guidelines for the Management of Patients with ST-Elevation Myocardial Infarction—Executive Summary: A Report of the American College of Cardiology/American Heart Association Task Force on Practice Guidelines (Writing Committee to Revise the 1999 Guidelines for the Management of Patients with Acute Myocardial Infarction," Circulation, vol. 110.5 pp. 588-636 (2004). DOI:10.1161/01.CIR.0000134791.68010.FA (Part3).
Lesnefsky, Edward J., et al. "Mitochondrial Dysfunction and Myocardial Ischemia-Reperfusion: Implications for Novel Therapies," Annual Review of Pharmacology and Toxicology, vol. 57 pp. 535-565 (2017).

(Continued)

*Primary Examiner* — Christina Bradley
(74) *Attorney, Agent, or Firm* — Hoffmann & Baron, LLP

(57) ABSTRACT

The present invention is related to the use of the growth hormone releasing peptide-6 (GHRP-6) for the manufacture of a late cardioprotective and cardiac restoration medicament. Said late cardioprotective and cardiac restoration medicament comprises GHRP-6 and a pharmaceutically acceptable excipient or vehicle. It also provides a method for the treatment of a disease that involves a low cardiac output, wherein a therapeutically effective amount of a late cardioprotective and cardiac restoration medicament comprising GHRP-6 is administered to a subject in need. Said medicament allows treating in a late manner, even days later, the myocardium that suffered episodes of stunning, hibernation, ischemia and its consequences thereof.

7 Claims, No Drawings

(56) References Cited

OTHER PUBLICATIONS

Banez, Borja, et al. "2017 ESC Guidelines for the Management of Acute Myocardial Infarction in Patients Presenting with ST-Segment Elevation: The Task Force for the Management of Acute Myocardial Infarction in Patients Presenting with ST-Segment Elevation of the European Society of Cardiology (ESC)," European Heart Journal, vol. 39.2, pp. 119-177 (2018). doi: 10.1093/eurheartj/ehx393 (Part1).

Banez, Borja, et al. "2017 ESC Guidelines for the Management of Acute Myocardial Infarction in Patients Presenting with ST-Segment Elevation: The Task Force for the Management of Acute Myocardial Infarction in Patients Presenting with ST-Segment Elevation of the European Society of Cardiology (ESC)," European Heart Journal, vol. 39.2, pp. 119-177 (2018). doi: 10.1093/eurheartj/ehx393 (Part2).

Banez, Borja, et al. "2017 ESC Guidelines for the Management of Acute Myocardial Infarction in Patients Presenting with ST-Segment Elevation: The Task Force for the Management of Acute Myocardial Infarction in Patients Presenting with ST-Segment Elevation of the European Society of Cardiology (ESC)," European Heart Journal, vol. 39.2, pp. 119-177 (2018). doi: 10.1093/eurheartj/ehx393 (Part3).

Crossman, David C., "The Pathophysiology of Myocardial Ischaemia," Heart. Vol. 90.5, pp. 576-580 (2004).

Heusch, Gerd, "Molecular Basis of Cardioprotection: Signal Transduction in Ischemic Pre-, Post-, and Remote Conditioning," Circulation Research, vol. 116.4, pp. 674-699 (2015). DOI: 10.1161/circresaha.116.305348 (Part1).

Heusch, Gerd, "Molecular Basis of Cardioprotection: Signal Transduction in Ischemic Pre-, Post-, and Remote Conditioning," Circulation Research, vol. 116.4, pp. 674-699 (2015). DOI: 10.1161/circresaha.116.305348 (Part2).

Portella, Rafael, et al., "Nitrite Confers Preconditioning and Cytoprotection After Ischemia/Reperfusion Injury Through the Modulation of Mitochondrial Function," Antioxidants & Redox Signaling, vol. 23.4, pp. 307-327 (2015) (Part1).

Portella, Rafael, et al., "Nitrite Confers Preconditioning and Cytoprotection After Ischemia/Reperfusion Injury Through the Modulation of Mitochondrial Function," Antioxidants & Redox Signaling, vol. 23.4, pp. 307-327 (2015) (Part2).

Zhu, J., et al., "Rapamycin Protection of Livers from Ischemia and Reperfusion Injury is Dependent on Both Autophagy Induction and Mammalian Target of Rapamycin Complex 2-Akt Activation," Transplantation, vol. 99, No. 1, op. 48-55 (2015).

Chandrika, Bhavya B., et al. "Endoplasmic Reticulum Stress-Induced Autophagy Provides Cytoprotection From Chemical Hypoxia and Oxidant Injury and Ameliorates Renal Ischemia-Reperfusion Injury," PLOS One, vol. 10, Issue 10, e0140025 (2015).

Kloner, Robert A., et al., "Clinical Cardiology: New Frontiers, Consequences of Brief Ischemia: Stunning, Preconditioning, and Their Clinical Implications, Part 1," Circulation, vol. 104, Issue 24, pp. 2981-2989 (Dec. 11, 2001). https://doi.org/10.1161/hc4801.1.00038.

Gibson, Michael C., "Editorial: Time is Myocardium and Time is Outcomes," Circulation, vol. 104, Issue 22, pp. 2632-2634 (Nov. 2001). https://doi.org/10.1161/circ.104.22.2632.

Berlanga, Jorge, et al. "Growth-Hormone-Releasing Peptide 6 (GHRP6) Prevents Oxidant Cytotoxicity and Reduces Myocardial Necrosis in a Model of Acute Myocardial Infarction," Clinical Science, vol. 112 pp. 241-250 (2007).

Shen, You-Tang, et al. "A Growth Hormone Secretagogue Prevents Ischemic-Induced Mortality Independently of the Growth Hormone Pathway in Dogs with Chronic Dilated Cardiomyopathy," Journal of Pharmacology and Experimental Therapeutics, vol. 306.2, pp. 815-820 (2003).

Cao, Ji-Min, et al., "Effects of Ghrelin and Synthetic GH Secretagogues on the Cardiovascular System," Trends in Endocrinology & Metabolism, vol. 17, No. 1, pp. 13-18 (2006).

Hamm, Christian W., et al., "Clinical Practice Guide for the Management of Acute Coronary Syndrome in Patients Without Persistence ST Segment Elevation", Rev. Esp. Cardiology, vol. 65, No. 2, pp. 173.e1-e55. (Google translation of Preamble and Introduction attached) (Part1).

Hamm, Christian W., et al., "Clinical Practice Guide for the Management of Acute Coronary Syndrome in Patients Without Persistence ST Segment Elevation", Rev. Esp. Cardiology, vol. 65, No. 2, pp. 173.e1-e55. (Google translation of Preamble and Introduction attached) (Part2).

Hamm, Christian W., et al., "Clinical Practice Guide for the Management of Acute Coronary Syndrome in Patients Without Persistence ST Segment Elevation", Rev. Esp. Cardiology, vol. 65, No. 2, pp. 173.e1-e55. (Google translation of Preamble and Introduction attached) (Part3).

Moreno, Pedro R., et al., "Myocardial Ischemia: Basic Concepts, Diagnosis and Clinical Implications. Part Two," Revista Colombiana de Cardiologla, vol. 23, No. 6, pp. 500-507 (2016). (English Abstract).

International Search Report corresponding to PCT/CU2019/05007 dated Jan. 20, 2020.

\* cited by examiner

USE OF GHRP-6 AS LATE CARDIOPROTECTIVE AND CARDIAC RESTORATION MEDICAMENT

This application is the U.S. National Phase of, and Applicant claims priority from, International Patent Application Number PCT/CU2019/050007 filed 19 Aug. 2019, which claims priority from CU 2018-0093 filed 21 Aug. 2018, each of which is incorporated herein by reference.

TECHNICAL FIELD

The present invention relates to human medicine, in particular to the use of the growth hormone releasing peptide-6 (GHRP-6) to restore the normal physiology of heart cells that have been subjected to long periods of hypoxia. This use of the peptide expands the window of therapeutic opportunity, transforming the paradigm that lethal non-return time occurs after the sixth hour of acute coronary events on development. The GHRP-6 promotes reversal of cytotoxic events resulting from ventricular dyskinesia and diastolic dysfunction in order to restore myocardial function and improve the perfusion of coronary, myocardium and the rest of the animal and human tissues and organs.

BACKGROUND OF INVENTION

Cardiovascular diseases remain at the top of the diseases that cause greater morbidity and mortality in the general population. In United States of America, occurs about 1.5 million cases of myocardial infarction per year; according to the Centers for Disease Control and Prevention (CDC), is the leading cause of mortality in that country. The World Health Organization (WHO) noted that in 2012, 17.5 million people died from cardiovascular disease, representing 31% of all deaths recorded in the world, and of these 7.4 million were due to Coronary Cardiopathy. More than three quarters of deaths from cardiovascular diseases come from Low and Middle Income Countries (Arós, F., Boraita, A., et al. Rev. Esp. Cardiol. 2000; 53: 1063-94).

In general, heart diseases are grouped as follows: Coronary Disease, Angina Pectoris, Myocardial Acute Infarct (MAI), Heart Failure, Congestive Heart Failure and Cardiomyopathies. Coronary heart disease leads to the establishment of ischemic heart disease, which is defined as the imbalance between myocardial oxygen demand and blood supply, as cited in World Health Organization (2015), Cardiovascular Diseases: http://www.who.int/en/news-room/fact-sheets/detail/cardiovascular-diseases-(cvds).

From all these diseases afore mentioned, the Acute Myocardial Infarct (AMI) reaches the highest rate of acute mortality. It occurs due to the sudden and sustained interruption of blood flow, causing the cells to die if irrigation is not restored soon. If the patient survives to a first attack, he is at risk of suffering another one within the next 6 months, or dying after associated complications thereof. Total recovery is hard to achieve after this first event, and specific treatment and care must be followed, since 5 out of 10 patients die during the first year after the infarction. Most coronary episodes constitute medical emergencies and urgencies; occur suddenly, with acute or overacute course, galloping involution of the patient, and unexpected. This presupposes the impossibility of predicting or anticipating an event of myocardial hypoxia.

The survival of cells in hypoxia depends on several factors, especially the duration of ischemia and the metabolic demand in question, according to the type of cell. Thus, the duration of the ischemia to which they have been subjected, at the time the restoration of blood flow occurs, is the main determinant of the success of reperfusion therapy. The shorter the ischemia time, the less the damage to the tissue, the less the damage at the time of reperfusion, and therefore, the lower number of associated subsequent complications.

Acute coronary syndrome is the operative term that describes a collection of clinical symptoms compatible with acute myocardial ischemia. Despite investigations by more than four decades, acute coronary events remain a leading cause of morbidity and mortality in many countries. The early mechanical or pharmacological reperfusion continues to be the paradigm, the golden rule, and apparently the only current alternative to rescue ventricular mass from necrosis before the ischemic/reperfusion. The most recent literature highlights the importance of practicing reperfusion during the first 12 hours of the onset of symptoms (European Society of Cardiology. Clinical practice guide for the management of acute coronary syndrome in patients without persistence ST segment elevation, Rev Esp. Cardiol. 2012; 65 (2): 173.e1-e55).

One of the major limitations in the prior art is the total absence of drugs that can be applied with therapeutic character, to acutely restore myocardial pump function, reduce its damage and restore systemic hemodynamic balance. This is because, most of the candidates developed up to date require prophylactic or pre-conditioning use, the intervention should be applied before the hypoxic event, which is not predictable. Blood thinners, platelet antiaggregants, antihypertensives and beta blockers drugs are aimed at maintaining adequate blood flow, to prevent obstructions and the resulting heart attacks, but not to restore the contractile mechanics and adequate cardiac output to the demands of the body.

Thus, another great limitations of the prior art is that myocardial hypoxia is not pharmacologically manageable until now, while the only possible option so far is limited to reducing its duration (Antman et al. Circulation 2004; 110: 588-636). This has implied a revolution in the measures of transfer, diagnosis, and early intervention of patients with any kind of acute coronary syndrome, at the time that the episode of AMI is globally the most known, frequent and investigated.

During myocardial hypoxia functional changes occur that include: i) the reduction of oxidative phosphorylation and of adenosine triphosphate (ATP) dependent membrane pumps, with subsequent influx of calcium, sodium and water to the cell; ii) the catabolism of ATP that leads to the accumulation of hypoxanthine with the generation of Reactive Oxygen Species (ROS) with the re-entry of $O_2$; iii) the promotion of the expression of proinflammatory gene products (leukocyte adhesion molecules, cytokines) and bioactive agents (endothelin, thromboxane A2) at the endothelial level; and iv) the repression of the products of some protective genes [constitutive nitric oxide synthase, thrombomodulin] and bioactive agents [Prostacyclin, Nitric Oxide] (Edward J. Lesnefsky, et al. Annual Review of Pharmacology and Toxicology; 2017, 57: 535-565).

As most acute coronary episodes cause damage to the myocardium in a very short period of time, until now it has been required to restore the coronary circulation within a period not exceeding 90 minutes (Gibsom M. Circulation. 2001; 104: 2632-2634). The most common example is that related to AMI, which requires a primary angioplasty in a time not exceeding 90 minutes, for the highest survival rate of the patient. In said conditions, not only fail the energy supply necessary for myocardial contraction, but the viability of the heart muscle is also affected. Coronary obstruction for only 20-30 minutes causes death zones that mainly affect the subendocardium. When the lack of irrigation is maintained, the entire thickness of the heart muscle is necrotized, causing what is known as transmural infarction. It is known that with a period of 6 to 12 hours the situation is irreversible, and leads to deterioration of the function of the left ventricle. It is recommended to perform all reperfusion intervention as urgently as possible, establishing the sixth hour after the onset of ischemia as a critical point for the myocardium (2017 ESC Guidelines. European Heart Journal 2018; 39: 119-177).

That is why another of the limitations of the current prior art is that no medication has been identified that allows expanding the currently narrow window of temporary opportunity to restore the functions of cardiomyocytes subjected to any kind of acute stress that leads to contractile abnormality. The relative mortality rate, in patients who have suffered an infarction, increases by 7.5% for every 30 minutes of treatment delay, and more than 90 minutes is too long to maintain cell life.

The limitations of the prior art are summarized as: (1) the limited time required by pharmacological candidates to be able to balance the ionic bases during hypoxia, (2) the absence of drugs capable of restoring an adequate contractile function of heart cells when ischemic stress implantation is over 120 minutes (2017 ESC Guidelines. European Heart Journal 2018; 39: 119-177), and finally, (3) the cascade of failures that have existed for 45 years in the search for late cardioprotectors or cytoprotectors, in general.

Many candidates have shown efficacy in animal models, but no benefit during their use in humans. In the case of the heart, said confronted limitations justify the well-known concepts of "door-to-balloon time", "time is myocardium," and "time is outcome" (David C. Crossman. Heart 2004; 90 (5): 576-580).

Summarizing, currently there is no drug intervention that can restore the cell function, exceeding the critical lethal point of non-return. This is corroborated by the long list of candidates that have failed after years of experimentation and investment of resources (Heusch G. Circulation Research 2015; 116: 674-699).

The most clear clinical testimony of prior art failures in early or late restoration of ventricular and hemodynamic function is the identification of the clinical entities of Stunned Myocardium and Hibernating Myocardium. These two entities are still lacking a specific and effective medication. In addition, both can happen in circumstances in which the coronary episode and the hypoxia have already been controlled (de Lima Portella Rafael, Lynn Bickta Janelle, and Shiva Sruti. Antioxidants & Redox Signaling 2015; 23 (4): 307-32; Zhu J, et al. Transplantation 2015; 99 (1): 48-55; Chandrika B B, Yang C, et al. PLoS ONE 2015; 10 (10): e0140025).

After a transient ischemia that did not cause irreversible damage, the myocardium may be "stunned", showing contractile dysfunction, which can be fully recovered or could go to a functional catastrophe. The mechanism is not fully known, but histological changes of sustained hypoxia can be detected several days after hypoxia has been overcome. It means that its mechanism is not understood, and that despite restoration of reperfusion, pump failure events may persist. The prior art knows no drugs that can abort this situation that can be lethal.

On the other hand, the hibernating myocardium is a myocardium viable but dysfunctional, since it is subjected to a chronic ischemia. The mechanisms are not known yet, but it is believed that coronary flow reserve is altered and repeated episodes of ischemia and myocardium stunning are generated. Numerous studies suggest that, if hibernation is extensive, there is the possibility of irreversible myocardial remodeling. Metabolically, there is an increase in glucose uptake and a reduction in the use of fatty acids.

The abrupt cessation or decrease of blood flow to the myocardium immediately generates a sequence of functional alterations: at 8 seconds the normal aerobic metabolism changes to anaerobic glycolytic metabolism; then, contractility decreases and later ceases; the action potential of the cell membrane decreases and electrocardiographic modifications appear.

Afterward, in the reversible phase of ischemia, only 20-25% of the existing ATP remains at the time of its onset. Phosphocreatine is then regenerated, and ATP levels stabilize, despite of the flow reduction. Lactate, together with $H^+$ ions, accumulates decreasing the pH to approximately 5.8, favoring the intracellular overload of osmotically active particles, which cause a mild degree of intracellular edema. The increase in intracellular $H^+$ causes $Na^+$ influx in the cell, through the $Na^+/H^+$ exchange. The excess of $Na^+$ induces $Ca^{++}$ entry through the $Na^+/Ca^{++}$ exchanger. When perfusion is restored, and if ischemia has been transitory, things return to normal.

There are circumstances in which, although perfusion has been restored, there has been no full contractile functional recovery. In these cases in which the heart has been "stunned", due to the impact produced by the ischemic episode, its full functional recovery will take from hours to days, or weeks. That is, there is adequate blood perfusion restored, but inadequate contractile function, implying inconsistency between perfusion and contractility. The myocardium stunning is the mechanical dysfunction that persists after the reperfusion, in spite of the absence of irreversible damage and restoration of normal or near normal blood flow. The essential points of the definition are: 1) the dysfunction after ischemia is a completely reversible abnormality, regardless of its severity or duration; and 2) the dysfunction is not caused by a primary failure of perfusion. In myocardial stunning, despite normal perfusion, contractile dysfunction occurs (Kloner R A, Jennings R B. Circulation 2001; 104: 2981-89).

Patent document WO2002053167A2, reveals the combination of Epidermal Growth Factor (EGF) and GHRP-6, which is useful in the prevention of tissue damage caused by ischemia. Nevertheless, the combination of said invention and all previously referred candidates must be administered under pre-conditioning prophylaxis schedules, or just immediately after the occurrence of ischemia, resulting its use and effectiveness conditioned to the narrow window time that up to now is valid. Mechanical interventions (conditioning), are also mentioned in the prior art, that activate endogenous mechanisms that lead to a better myocardial protection against damage caused by a prolonged ischemic event and subsequent reperfusion. The conditioning is based on repeated inflation-deflation cycles of the arterial vessel. The preconditioning consists in the application of short cycles of ischemia-reperfusion previous to the event of prolonged ischemia. The ischemic post-conditioning strategy is based on the use of ischemia-reperfusion cycles when initiating reperfusion.

Therefore, there is still interest in finding late cardioprotective drugs, that allow to expand the narrow window of treatment opportunity, to restore and reestablish the cardiac functional homeostasis.

DESCRIPTION OF THE INVENTION

This invention contributes to solve the aforementioned problem, disclosing the use of the GHRP-6 in the manufacture of a late cardioprotective and cardiac restoration medicine. For the first time, a pharmacological agent able to restore cell homeostasis and function of cardiac tissue, for long hours or even days, of an established ischemic process, regardless of the current narrow time window that impose the biology of the system itself, and able to restore the cellular metabolism has been identified. In this way, the window of opportunity for treatment and, therefore, the possibility for therapeutic success is extended.

The invention is based on the use of GHRP-6 as an active pharmaceutical ingredient capable of restoring cardiomyocytes function, in late scenarios of acute or chronic, mild or severe, acute or terminal ventricular failure. The treatment ensures that a set of molecular processes that involve the salvation route known as RISK (Reperfusion Injury Salvage Kinase) get activated. In addition, it restores the function of ionic pumps, and reduces inflammation, wall stress, and the formation of reactive oxygen species.

For the purposes of the invention, the term "cardioprotective medicine" refers to a drug capable of rescuing cardiomyocytes from cell death, in scenarios that otherwise were lethal, being able to maintain energy homeostasis, the stability of ionic pumps, to guarantee conduction and rhythm, as well as to maintain the contractile function of such types of cells.

The term "cardiac restoration medicine", as used in this invention, refers to a medicament capable of reversing the deterioration of myocardial mechanical function, without increasing heart rate, oxygen consumption, cardiac output, or at the cost of reducing diastole time.

GHRP-6, as an active pharmaceutical ingredient is applied with therapeutic purposes, even belatedly in all said subjects with myocardial damage or dysfunction due to hibernation or ventricular remodeling. It can also be applied to subjects undergoing coronary revascularization interventions, in which the oxygenation of one or several organs is necessarily compromised, due to total or partial ischemia, and then reperfusion is performed. It is also applicable in the control and prevention of the consequences of thromboembolic phenomena. Even more relevant, the treatment is applicable to those who are revascularized and who cannot recover the contractile function of the ventricle and progress to systolic and diastolic dysfunctions.

Therefore, in an embodiment of the invention, the cardioprotective and cardiac restoration medicament that comprises GHRP-6 is administered to patients affected by a pathology selected from the group comprising: AMI with elevation or depression of ST segment, acute coronary syndrome, acute or chronic myocardial ischemic disease, heart failure and ischemia/reperfusion episodes of the cardiac muscle, to rescue ventricular mass from stunning or hibernation, low cardiac output syndrome and cardiogenic shock.

The use of GHRP-6 may be the only pharmacological option to control stunning and hibernation, which can ultimately lead to heart failure syndrome and to death. The compassionate use of GHRP-6 has shown to be useful in critically ill patients with Grade IV Heart Failure, and in others already waiting for an appropriate donor for heart transplantation. It presupposes the rupture of two paradigms: (1) Rupture of the golden rule that "time is myocardium", in the way that the time elapsed in the implantation of the damage is already irrelevant as opposed to the efficacy of the medication; (2) Stunning, hibernation, low output and severe heart failure are already pharmacologically manageable. These are clear advantages of this invention. Therefore, in another embodiment, the late cardioprotective and cardiac restoration medicament of the invention is administered to patients awaiting a heart transplant, to correct and optimize their systemic homeostasis and health status, in general.

In one embodiment, the late cardioprotective and cardiac restoration medicament comprising GHRP-6 is administered by peripheral intravenous, central or within the coronary tree. In a particular embodiment, said medicament is administered as part of the endoluminal dilatation procedure. The GHRP-6 can be administered by repeated injections or by continuous infusion systems. It includes intravenous and arterial administrations, including instillation within the coronary tree before or during reperfusion by balloon or "stent". The versatility of the mechanisms of action of this agent justifies its administration to a wide range of patients who have suffered coronary episodes, any kind of cardiomyopathies, and regardless of the time of initiation of treatment and its extension. The merit of the treatment is to restore the function of the impaired heart, in an acute or stunned condition, and even beyond the so-called critical time or point of no return.

In another scenario, the treatment can be applied therapeutically to graft recipients, to allow a proper conditioning of the host organism and the transplanted organ. Patients with grade IV functional class and with transplant criteria have been treated, resulting in a rise of the left ventricle mechanical function and they have reached the transplant under conditions of better systemic tissue oxygenation. It can be administered repeatedly, after the transplant is performed, and treatment can begin in the operating room, once the circulation between the recipient and the grafted organ has been established.

In an embodiment of the invention, the medicament comprising GHRP-6 is administered in such a way that the patient receives between 25 and 200 μg of peptide/kg of body weight, in bolus form. The restorative effect of this treatment on the ischemic heart makes an option the concomitant administration of any antioxidant agent, of iron chelating compounds, as well as of enzymes involved in the anti-oxidant defense.

In another aspect, the invention provides a late cardioprotective and cardiac restoration medicament comprising the GHRP-6 and a pharmaceutically acceptable vehicle or excipient. Due to its effect, late cardioprotective medicament comprising GHRP-6 can be administered 12 or more hours after the implantation of an episode of ischemia. In a particular embodiment, said medicament is administered between 13 and 96 hours after the implantation of an episode of ischemia.

The late cardioprotective and cardiac restoration medicament of present invention may be concomitantly administered with thrombolytic or fibrinolytic agents, referred to as plasminogen activators, and in the event of reperfusion induced by mechanical methods, including angioplasty. Said medicament could be applied along, previously or subsequently to pre- and post-conditioning maneuvers.

It is recommended to use concentrations ranging from 25 to 400 μg/ml, in vehicles such as physiological saline (0.9% sodium chloride); Ringer Lactate solution; plasma; albumin;

and dextrose; isotonics or their mixtures. The routes of administration may be deep or peripheral intravenous, intraarterial or intraperitoneal. The administration of the drug of the invention can be repeated twice to three times a day.

In the invention, GHRP-6 is administered, as late cardioprotective and cardiac restoration medicine, to patients with episodes of ischemia/reperfusion of the heart muscle, to correct the central and peripheral hemodynamics, stabilize the central venous pressure and the mean arterial pressure, as well as to eliminate vasoplegia and vascular resistance. In addition, it is administered to patients with lactic acidosis derived from states of low cardiac output, hypovolemia, ventilatory failure, increased preload.

In another aspect, the invention discloses a method for the treatment of a disease that involves a low cardiac output wherein a therapeutically effective amount of a late cardioprotective and cardiac restoration medicament comprising GHRP-6 is administered to a subject in need thereof.

In an embodiment of the invention, the method is applied to patients suffering a pathology selected from the group consisting of AMI with elevation or depression of ST segment, acute coronary syndrome, acute or chronic ischemic myocardial disease, heart failure, episodes of ischemia/reperfusion of the heart muscle, to rescue the ventricular mass from states of stunning or hibernation, low-cardiac output syndrome and cardiogenic shock. In another embodiment, the method is applied to patients awaiting a heart transplant, to correct and optimize their systemic homeostasis and health status, in general.

EXAMPLES

Example 1. Demonstration of the Effect of GHRP-6 on the Extension of the Window of Therapeutic Opportunity for the Rescue of Myocardial Mass Under Coronary Occlusion. Experimental Model With and Without Reperfusion The pharmacological manipulation, to reduce the size of the infarction, has not yielded the expected results, despite 45 years of incessant research. The sudden character of the ischemic episode contributes to this and, especially, the short time available to rescue ventricular mass from death when ischemia has been implanted.

The objective of the study was to evaluate, and to compare, the therapeutic impact of the late administration of GHRP-6 on functional parameters of the left ventricle, regarding the effect of the peptide acutely administered. Another objective was to assess the effect of late treatment in a group of animals in which the reperfusion was not performed.

The implementation of the AMI was performed in female pigs of the Yorkshire breed, with body weight of 22-27 kg. The anesthesia was induced with propofol, midazolam and pancuronium, by intravenous route. Under general anesthesia, obtained with a mixture of isofluorane/oxygen and nitrous oxide the ischemia was provoked. It was induced by a thoracotomy between the fifth and sixth intercostal spaces, until reaching the left circumflex artery, which was occluded by a 30 mm arterial clamping for one hour. Immediately, the record of the electrocardiogram and the heart rate was taken, every 20 seconds. At the end of 60 minutes of occlusion, the clamping was released, and so began the reperfusion phase, to complete the 10 days after ischemia. For the experimental group without reperfusion, that simulates the state called as non-reflux, a permanent ligation of the circumflex artery, with surgical thread, was performed. Both procedures, clamping and permanent ligation, induce an AMI with a ST Segment elevation. The recording of heart rate and electrocardiogram continued until the superficial suture of the thorax. The animals were sacrificed, by exsanguination, on the tenth day after the ischemia episode was induced. Under an anesthetic overdose, the determination of the area of the AMI was made, by means of the calculation of the area at risk with Evans blue.

For the echocardiographic evaluation, the pigs were previously sedated with a mixture of propofol/midazolam. A Kontron ultrasound system, Sigma 1 AC Cardio model, equipped with 3.5-7.5 MHz mechanical-cardiac sector transducers was used.

The parameters evaluated were the following:

Left Ventricle Ejection Fraction (LVEF), estimated by the Teich method.

Left Ventricle Tele-Systolic and Tele-diastolic Pressures.

Infarction Area, estimated on the area at risk (%).

The study design, in terms of the experimental groups used, is summarized in Table 1. Seven animals per group were used. In all groups, the animals received treatment every 12 hours, for 10 days after ischemia. The administrations of GHRP-6 or placebo were performed through a central catheter. In the case of the groups that received the peptide, it was diluted in 10 ml of physiological saline. The essence of the study was to evaluate the influence of the time of initiation of treatment on functional parameters and size of the ventricular not viable territory.

TABLE 1

Experimental design.

| Group | Onset of treatment |
|---|---|
| 1. Physiological saline (Placebo) | Immediately at the beginning of reperfusion |
| 2. GHRP-6 (400 µg/kg) | Immediately at the beginning of reperfusion |
| 3. GHRP-6 (400 µg/kg) | 72 hours after the start of reperfusion |
| 4. GHRP-6 (400 µg/kg) | 5 days after the start of reperfusion |
| 5. No reperfusion (GHRP-6 400 µg/kg) | One hour after the artery was permanently clamped and after the occurrence of an elevation in the ST segment. |

The response to treatment with GHRP-6, administered at different times after reperfusion, is reflected in Table 2. The evaluation of the effect of the treatment on the control of the infarct size as well as variables describing the function and state of the left ventricle are included. The results indicate that, even if the treatment is started 72 hours after restoration of blood flow (reperfusion), GHRP-6 is able to significantly reduce the size of myocardial infarction by 13%, approximately, in comparison to placebo. There were no significant statistically differences between the effect of intervention with GHRP-6 in parallel to reperfusion and the one achieved when the treatment started 72 hours later. Although more discreetly, the latest treatment, initiated on the 5th day after ischemia, still rescue from death an 8% of the ventricular territory corresponding to the area at risk. The result of opening a window of therapeutic opportunity in the non-reperfused or non-reflux group was even more surprising.

TABLE 2

Response variables to treatment.

| Experimental Group | Infarction Area (%) | *LVEF (%) | LV* telediastolic pressure (mmHg) | LV telesystolic pressure (mmHg) |
|---|---|---|---|---|
| Basal conditions | Not applicable | 81 ± 2.8 | 3.3 ± 1.7 | 89 ± 2.3 |
| Group 1 | 48.7 ± 2.6 | 38 ± 3.6 | 9.5 ± 2.2 | 68 ± 4.2 |
| Group 2 | 31.6 ± 5.2 | 80 ± 2.5 | 4.6 ± 1.1 | 80 ± 2.2 |
| Group 3 | 35.4 ± 6.4 | 77 ± 4.1 | 4.4 ± 1.6 | 81 ± 3.0 |
| Group 4 | 37.0 ± 4.3 | 60 ± 6.6 | 5.2 ± 0.8 | 77 ± 3.1 |
| Group 5 | 36.1 ± 2.8 | 72 ± 5.5 | 5.1 ± 1.9 | 80 ± 2.6 |

**LV: Left Ventricle

Even with no rescue effect associated to the phenomenon of reperfusion, the treatment with GHRP-6 reduced by 12% the area of ventricular death. Corresponding to the effect of anti-necrogenic rescue still late, it is notorious the impact of the treatment on the preservation of LVEF. The AMI caused a 43% decrease in LVEF in the placebo group, 10 days after the episode. However, in the most astringent context, associated to the start of treatment with GHRP-6 on the fifth day, the deterioration of ventricular function only declines by 21%, compared to the study in baseline physiological conditions. In other words, 22% of the LVEF is rescued in the group that began to be medicated 5 days after the ischemic event. Similarly, the effect of treatment with GHRP-6 in the non-reflux group is also surprising. Even without reperfusion, the treatment prevents cell death and guarantees the function of pump of the left ventricle with only 9% difference with the data derived from baseline conditions.

On the other hand, the GHRP-6 supports the parameters of telesystolic and telediastolic pressures in a way similar to those determined in baseline physiological conditions. There is a significant reduction in diastolic pressure in all the groups that received the GHRP-6, regardless of when the treatment started, when compared to the placebo group. In concordance, the treatment manages to maintain the intra-cavity pressure at the end of the systole much higher than that determined for the placebo group. In other words, the treatment prevents the acute ventricular pump failure or the low cardiac output syndrome.

It can be concluded that the treatment with GHRP-6 showed a surprising and unusual ability to expand the window of therapeutic opportunity in episodes of ischemia and heart reperfusion, such as those associated to AMI. In addition, the treatment with GHRP-6 showed a surprising and unusual ability to restore cardiac cell homeostasis, as well as its vital functions, in the most pathogenic of the scenarios that is in the non-reperfusion states. It establishes a new property, the ability to expand the window of functional opportunity. Also, it was evidenced that the treatment aborts the phenomenon of ventricular stunning associated to ischemia. Additionally, an AMI with five days of evolution appears, for the first time, as a scenario pharmacologically manageable with GHRP-6, restoring functional homeostasis in a proper way.

As infarct progresses as "a wavefront" from the subendocardium to the epicardium, it is possible to abort this wave progress toward death, by widening the window of therapeutic opportunity for reperfusion or other required pharmacological interventions. It is shown, for the first time, that is possible to establish homeostasis of the heart muscle even when days have elapsed since the onset of the ischemic episode. This finding constitutes an unprecedented milestone in medicine.

Example 2. Extension of the Therapeutic Opportunity Window for the Functional Restoration of Myocardium in Patients with Acute Infarction Treated with GHRP-6

Elements of clinical response in patients who suffered a myocardial infarction with elevation of the ST segment, treated with GHRP-6 in an acute or a delayed way are shown here below.

First cohort. Comprising 19 patients over 30 years old, of both sexes, with a diagnosis of AMI with ST segment elevation, all with occlusion of the anterior descending artery, first episode, who arrived at a cardiology department before 12 hours of implantation of the precordial pain. The average door-ball time was 6 hours. All patients received primary percutaneous transluminal angioplasty, and immediately after the culprit artery flow was restored they received treatment with GHRP-6. In some patients, the treatment was performed by intra-coronary flushing, after the flow was restored. Residual lesions occupied less than 25% of the initial occlusion area, so it was considered as a TIMI 3, according to the Coronary Risk Score known as TIMI. In other cases, the first administration was performed by a central-venous route, just at the time of reperfusion, in the hemodynamic room. GHRP-6 was administered at a dose of 100 µg/kg of body weight, twice a day, for 7 days, time spent in the coronary intensive care hospital room. Clinical, echocardiographic and scintigraphy perfusion imaging evaluation were performed 30 days after the episode of ischemia.

Second cohort. Comprising 13 patients over 30 years old, of both sexes, with a diagnosis of AMI with elevated ST segment, who received percutaneous transluminal angioplasty before 12 hours of implantation of precordial pain. All these patients evolved in an unfavorable way, and with uncertain prognosis between 24 and 96 hours after a successful endoluminal reperfusion, according to the imaging criteria all were considered as TIMI grade 3. Hypothetically, this apparent success of reperfusion associated with a ventricular dysfunction, reminiscent of myocardial stunning, may be due to two phenomena, the non-restoration of circulation at the microcapillary system level, suggesting the persistence of ischemia/tissue hypoxia; or the existence of true stunning considering a TIMI 3, with poor ventricular contractility.

These patients had a galloping evolution, from low-cardiac output syndrome to cardiogenic shock. This led to the decision of establishing an alternative treatment with GHRP-6, to try to reduce dyskinesia of the ventricular musculature, to attenuate the process of presumed stunning, to dampen hypoxia, and to rescue from death a territory of ischemic ventricular mass. The patients who implanted a reinfarction received rescue angioplasty. One of these patients died during the procedure. None of the patients met criteria for the coronary revascularization practice. A summary of the characteristics of the patients in that second cohort is shown in Table 3. In these cases, the first administration of the peptide was carried out at least after 48 hours of torpid evolution after a TIMI 3. During the treatment time, the GHRP-6 was administered intravenously, every 12 hours.

TABLE 3

Demographic characterization and evolution of the
patients in the second cohort.

| Patient | Sex/Age | PTA Time | Evolution between 3 and 7 days |
|---|---|---|---|
| RGD | F/65 | 6 hours | LCOS |
| AFP | M/49 | 4 hours | CS |
| YRH | M/71 | 11 hours | CS |
| PPL | M/62 | 7 hours | LCOS |
| ICR | F/70 | 10 hours | CS + SIRS |
| JIM | F/66 | 11 hours | LCOS + CS |
| AMG | M/72 | 9 hours | CS |
| CVP | M/59 | 10 hours | CS + SIRS |
| CSC | M/51 | 4 hours | Reinfarction. Patient died |
| AEA | F/66 | 8 hours | LCOS |
| MPS | M/65 | 10 hours | CS |
| NSS | F/60 | 6 hours | Reinfarction at 24 hours. |
| YMM | M/55 | 6 hours | Reinfarction on the third day. |

PTA: Percutaneous Transluminal Angioplasty, LCOS: Low Cardiac Output Syndrome, CS: Cardiogenic Shock, SIRS: Systemic Inflammatory Response Syndrome.

Results of the Study

The patients of the first cohort, who received the GHRP-6 after a successful percutaneous transluminal angioplasty with reperfusion considered as TIMI 3, exhibited a favorable evolution, without further important complications. The initial and evolutionary echocardiographic parameters are shown in Table 4 (useful data derived from 15 patients). It is worth noting the response to treatment with GHRP-6, compared to the natural evolution of the disease, if the standard values taken as a reference in international literature are considered (Pedro R. Moreno and Juan H. del Portillo. Rev Colomb. Cardiol. 2016; 23 (6): 500-507; 2017 ESC Guidelines. European Heart Journal 2018; 39: 119-177).

TABLE 4

Parameters measured by echocardiography performed to patients with AMI
with ST segment elevation receiving GHRP-6 in an early manner.

| Time of Scanning | SPWT (mm) | SST (mm) | Telesystolic volume (ml) | Telediastolic volumen (ml) | LVEF % | SSF % |
|---|---|---|---|---|---|---|
| Start of treatment. Minutes after the PTA. | 10.1 ± 2 | 10.6 ± 3, 1 | 77 ± 12 | 81 ± 14 | 38 ± 5.9 | 27 ± 2.6 |
| 30 days after PTA | 11.6 ± 0.7 | 10.3 ± 1.6 | 65 ± 23 | 87 ± 11 | 51 ± 8.6 | 35 ± 6.5 |
| 90 days after PTA | 11.3 ± 1.8 | 10.7 ± 1 | 49 ± 8 | 111 ± 16 | 57 ± 6.6 | 42 ± 9.6 |

PTA: Percutaneous Transluminal Angioplasty;
SPWT: Systolic Posterior Wall Thickness. Reference value (9.8-11.2 mm);
SST: Systolic Septum Thickness, Reference value (8.6-11.7 mm), LVEF. Reference value (40-85%);
SSF: Septum Shortening Fraction. Reference value (28-42%), Telesystolic Volume. Reference value (12-60 ml), Telediastolic Volume. Reference value (120-140 ml).

It was found that patients treated with GHRP-6 showed progressive improvement over time. In all these cases, a physiological functional restitution was achieved, which is described below: There were no variations in morphological constants such as SPWT and SST. There was a progressive reduction of telesystolic volume, implying an improvement in pump function of the left ventricle, improving cardiac function and conservation of functioning cavities and the response of the wall, expressed normal levels of afterload. It was observed a progressive and stable increase of telediastolic volume, suggesting an improvement in diastolic dysfunction, increasing in extension of the left ventricle walls. In other words, better ventricular relaxation, with the subsequent increase in afterload. Finally, two nearby parameters, LVEF and AF, showed a steady increase, reaching normal levels at 90 days. This means a total correction of the segmental and global kinetics of the left ventricle function.

Regarding the patients of the second cohort, who received treatment with GHRP-6 administered in a late manner, Table 5 shows the outcome, as well as the echocardiographic characterization, performed at 90 days of evolution.

TABLE 5

Outcome and evolutionary results of the second
cohort. Late treatment with GHRP-6.

| Patient | GHRP-6 intervention | Dose | Outcome | Echocardiographic characterization |
|---|---|---|---|---|
| RGD | Day 3 to 9 | 100 µg/kg | Elevation of LVEF after 72 hours of treatment. Exit of the low-cardiac output syndrome. | Non-contractile area of 12% of the left ventricle. LVEF of 63%. |
| AFP | Day 3 to 9 | 100 µg/kg | Elevation of LVEF. Increase in diuresis. | Non-contractile area of 21% of the left ventricle. LVEF of 48%. |
| YRH | Day 4 to 10 | 100 µg/kg | Elevation of LVEF. Disconnect the mechanical ventilation on the fifth day. | Non-contractile area of 20% of the left ventricle. LVEF of 50%. |
| PPL | Day 2 to 8 | 100 µg/kg | Elevation of LVEF after 72 hours of treatment. | Non-contractile area of 3% of the left ventricle. LVEF of 50%. |

TABLE 5-continued

Outcome and evolutionary results of the second
cohort. Late treatment with GHRP-6.

| Patient | GHRP-6 intervention | Dose | Outcome | Echocardiographic characterization |
|---|---|---|---|---|
| ICR | Day 3 to 9 | 200 µg/kg | Elevation of LVEF after 72 hours of treatment. Hemodynamic stability. | Non-contractile area of 17% of the left ventricle. LVEF of 47%. |

TABLE 5-continued

Outcome and evolutionary results of the second cohort. Late treatment with GHRP-6.

| Patient | GHRP-6 intervention | Dose | Outcome | Echocardiographic characterization |
|---|---|---|---|---|
| JIM | Day 4 to 10 | 200 μg/kg | Elevation of LVEF after 72 hours of treatment. Hemodynamic stability. Increase in diuresis | Non-contractile area of 19% of the left ventricle. LVEF of 51%. |
| AMG | Day 4 to 10 | 100 μg/kg | Elevation of LVEF after 48 hours of treatment. Hemodynamic stability | Non-contractile area of 13% of the left ventricle. LVEF of 52%. |
| CVP | Day 4 to 10 | 200 μg/kg | Elevation of the LVEF at 48 hours. Hemodynamic stability and diuresis on the fifth day post-treatment. | Non-contractile area of 23% of the left ventricle. LVEF of 46%. |
| AEA | Day 3 to 9 | 100 μg/kg | Elevation of the LVEF 48 hours after the GHRP-6 started. Hemodynamic stability and diuresis achieved on the fifth day of treatment. | 7% non-contractile area of the left ventricle. LVEF of 56%. |
| MPS | Day 4 to 10 | 100 μg/kg | Elevation of LVEF after 48 hours of treatment with GHRP-6. Hemodynamic stability with suspension of dobutamine and epinephrine on the fourth day of treatment. | Non-contractile area of 23% of the left ventricle. LVEF of 45%. |

Patient CSC died during the angioplasty rescue procedure. Once the treatment with peptide was started, the suspension of vasopressor amines was achieved in 8 out of 10 patients evaluated, in an interval that was close to 96 hours. Of the 12 surviving patients, 10 were evaluated by echocardiography at the third month after AMI. It was surprising the response to the late treatment with GHRP-6 in all these patients. The major medical findings in these 10 patients demonstrate that treatment with said peptide favored survival, by widening the management and pharmacological intervention window in a comprehensive way. The non-existence in this technical field of a similar treatment brings an unquestionable novelty to this method of treatment.

Concerning the 13 critical patients, 12 of them survived. At commencement of the study, all these patients showed very unfavorable evolution, with life threatening, despite a successful reperfusion maneuver, according the monitoring imaging criteria. The evolution towards low cardiac output syndrome, and cardiogenic shock, indicates that the pump function of left ventricle was not recovered, or that a severe and sustained ventricular stunning pattern was implanted. This implies the persistence of distal, partial, or even normoxia ischemia but with sarcomeric dysfunction. The treatment with GHRP-6 helped to stabilize the central and peripheral hemodynamics as well as the ejector function and cardiac output, reducing the supra-ventricular tachycardia, and increasing the ejection fraction. In addition, the treatment with GHRP-6 restored the glomerular filtrate, and diastolic function, reducing preload and venous pressures.

Unexpectedly, the echocardiographic study conducted 90 days after the AMI with ST segment elevation shows dramatically favorable values of ejection fraction, of global contractility of the left ventricle and the septum. As it is shown in Table 6, 90 days after treatment with GHRP-6, the group treated in a late manner exhibited a LVEF close to 51%, which is unexpectedly favorable. Accordingly, the treatment with GHRP-6 favored the cell restoration, even when treatment began lately. All patients were treated with GHRP-6 at least 48 hours after developed complicated clinical conditions of hemodynamic instability and extra cardiac-dysfunctions were established. Therefore, it is demonstrated that the treatment with GHRP-6 significantly and unexpectedly expands the window of therapeutic opportunity for the restoration of cardiovascular functions in infarcted patients with life-threatening complications.

TABLE 6

LVEF values determined 90 days after treatment with GHRP-6.

| Cohort | LVEF %. Mean ± SD |
|---|---|
| Cohort 1. Acute treatment | 57.0 ± 6.61 |
| Cohort 2. Late treatment | 50.8 ± 5.34 |

Example 3. Clinical Demonstration of the Extension of the Therapeutic Opportunity Window in Patients with Grade IV Heart Failure Included in the Transplant Pool and Treated with GHRP-6

This is a cohort of 7 patients, who received the compassionate treatment with GHRP-6, under informed consent. All patients were in advanced heart failure, evaluated as functional class grade IV, according to the scale of the New York Heart Association. These patients were hospitalized in specialized cardiology services of two hospitals, and the ischemic heart disease, the idiopathic dilated cardiomyopathy, the heart valve disease, and the postpartum dilated cardiomyopathy were considered as the underlying condition for heart failure. All patients evaluated had a significant limitation in functional capacity, were permanently bedridden at 45° Fowler position, with advanced cardiac dysfunction, and LVEF values below 25%. They had minimal effort dyspnea, inability to adequately fulfill the 6 minutes' walk test, and instability in fluid balance and renal function, despite the diet control and the treatment with diuretics, the restriction of salt and the monitoring body weight.

All patients received between 50 and 200 μg of GHRP-6/kg body weight, two or three times a day, according to medical criteria, by intravenous route. All treatments were performed while the patients were awaiting for heart transplantation. The treatment period with GHRP-6 was between 25 days and 30 days per cycle.

A cycle of treatment with GHRP-6 was performed every three months. The maximum was three cycles. All patients were maintained with previous medical treatments, based on digital, diuretics, renin-angiotensin-aldosterone axis inhibitors (neurohormones) and pressor amines when required. Table 7 summarizes initial and final (after treatment) values for each parameter.

TABLE 7

Comparison of parameters evaluated before and after treatment in grade IV heart failure patients.

| Patient | 6 minute's test (min)* | Systolic volume* | Cardiac output (L/m)* | Oxygen consumption (ml/kg/min)* | LVEF %* |
|---|---|---|---|---|---|
| AMJ | 2/23 | 25/47 | 2.1/2.89 | 4.2/6.6 | 22/31 |
| BLP | 41/201 | 27/51 | 1.98/3.2 | 3.63/9.5 | 18/26 |
| BCC | 38/258 | 29/50 | 3.2/4.3 | 4.12/7.7 | 20/28 |
| IBP | 27/198 | 30/54 | 2.7/3.8 | 3.91/7 | 19/30 |
| NFG | 39/179 | 29/60 | 1.89/2.9 | 3.05/6.4 | 21/29 |
| MGT | 29/221 | 31/56 | 2.17/3.2 | 4.1/7.2 | 20/23 |
| JSA | 35/175 | 35/49 | 2.41/3.08 | 3.87/7.6 | 21/25 |

*Before treatment values/after treatment values

Compassionate treatments, performed on patients incorporated into the transplant pool, were applied to individuals in cardiovascular catastrophe with Grade IV heart failure. This presumes the harshest scenario for a pharmacological response, given the unfavorable prognosis involved in the process. The treatment was applied to patients with slight multiple organ dysfunction, due to its high degree of hemodynamic mismatch and systemic hypoxia.

Despite this marked morbidity and co-morbidity, an unusual response was observed. As it is shown in Table 7, the treatment was able to restore cardiac, hemodynamic, ventilatory and clinical constants. The treatment showed that, regardless of the stage of cardiovascular and systemic deterioration, it is possible to correct homeostasis, and therefore vital parameters and functions. This evidence has no precedent in medical practice.

What is claimed is:

1. A method for the treatment of a disease that involves a low cardiac output, said method comprising administering to a human in need thereof a therapeutically effective amount of a late cardioprotective and cardiac restoration medicament comprising the growth hormone releasing peptide-6 (GHRP-6), wherein the medicament is first administered at least 12 hours after an episode of ischemia is established.

2. The method according to claim 1 wherein the medicament is administered to patients affected by a pathology selected from the group consisting of acute myocardial infarction (AMI) with elevation or depression of the ST segment, acute coronary syndrome, acute or chronic ischemic myocardial disease, heart failure, episodes of ischemia/reperfusion of the heart muscle, to rescue ventricular mass from stunning or hibernation states, low-cardiac output syndrome and cardiogenic shock.

3. The method according to claim 1 wherein the medicament is administered to patients awaiting a heart transplant to correct and optimize the systemic homeostasis and general state of health.

4. The method according to claim 1 wherein the medicament is administered by central intravenous route, peripheral intravenous route or within the coronary tree.

5. The method according to claim 4 wherein the medicament is administered as part of an endoluminal dilation procedure.

6. The method according to claim 1 wherein the GHRP-6 is administered at 25-200 μg/kg of a patient's body weight as a bolus.

7. The method according to claim 1 wherein the medicament is first administered between 13 and 96 hours after an episode of ischemia is established.

* * * * *